United States Patent
Kasahara et al.

(10) Patent No.: US 8,004,270 B2
(45) Date of Patent: Aug. 23, 2011

(54) INSPECTING APPARATUS FOR PHOTOVOLTAIC DEVICES

(75) Inventors: Masato Kasahara, Okazaki (JP); Toshio Shibuya, Okazaki (JP)

(73) Assignee: Nisshinbo Industries, Inc., Tokyo (JP)

(*) Notice: Subject to any disclaimer, the term of this patent is extended or adjusted under 35 U.S.C. 154(b) by 42 days.

(21) Appl. No.: 12/255,399

(22) Filed: Oct. 21, 2008

(65) Prior Publication Data

US 2009/0102453 A1  Apr. 23, 2009

(30) Foreign Application Priority Data

Oct. 22, 2007 (JP) .................................. 2007-273538

(51) Int. Cl.
*G01N 21/00* (2006.01)

(52) U.S. Cl. .................... 324/96; 324/750.03; 356/237.2
(58) Field of Classification Search ............... 356/237.2; 324/96, 750–752, 767
See application file for complete search history.

(56) References Cited

U.S. PATENT DOCUMENTS

| 7,528,615 | B2 * | 5/2009 | Shimotomai | 324/752 |
| 7,601,941 | B2 * | 10/2009 | Fuyuki | 324/752 |
| 2010/0150428 | A1 * | 6/2010 | Andreev et al. | 382/145 |

FOREIGN PATENT DOCUMENTS

| JP | 02-031175 A | 2/1990 |
| JP | 06-097508 A | 4/1994 |
| JP | 2007-088419 A | 4/2007 |
| WO | 2006-059615 A1 | 6/2006 |
| WO | 2007-129585 A1 | 11/2007 |

* cited by examiner

*Primary Examiner* — Gregory J Toatley
*Assistant Examiner* — Iyabo S Alli
(74) *Attorney, Agent, or Firm* — Westerman, Hattori, Daniels & Adrian, LLP

(57) ABSTRACT

The present invention provides an inspecting apparatus for photovoltaic devices which electrifies the photovoltaic devices in a forward direction thereof to make the photovoltaic devices emit electro-luminescence light and which has a simple-structured and cheap darkroom. The inspecting apparatus of the present invention includes a darkroom 110 provided with a flat upper surface 111, a transparent plate 112 which is provided in the upper surface of the darkroom for disposing the photovoltaic devices as an inspecting object 200, a camera 120 which is provided in the darkroom and a driving mechanism to move the camera in the darkroom.

4 Claims, 9 Drawing Sheets

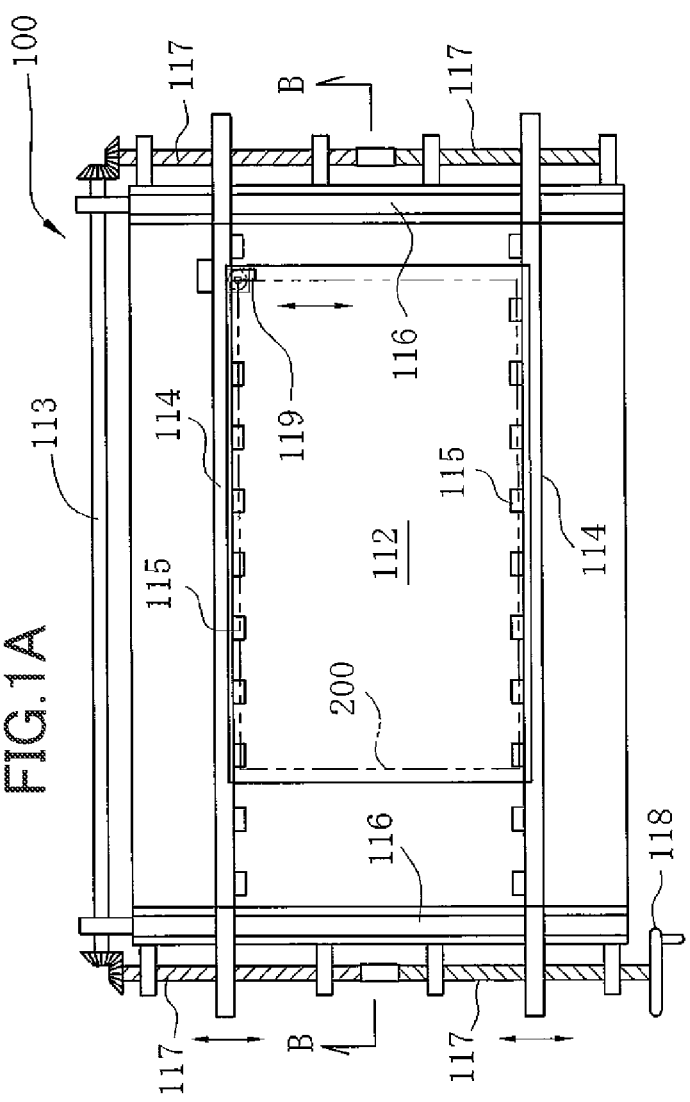
FIG.1A
FIG.1B
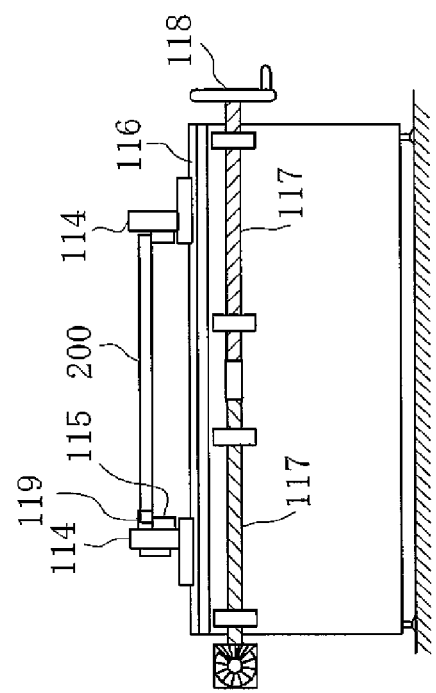
FIG.1C

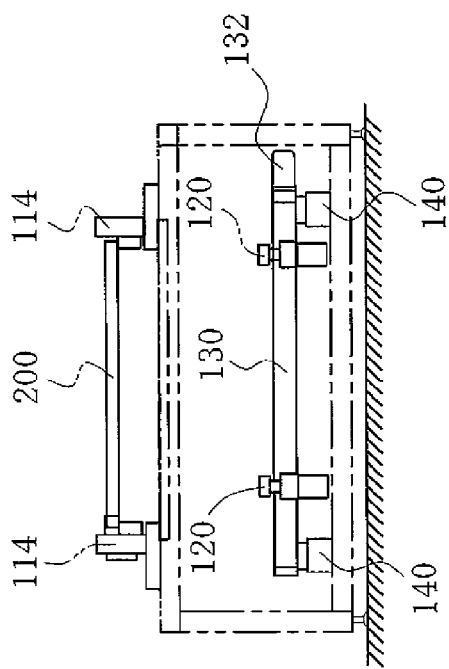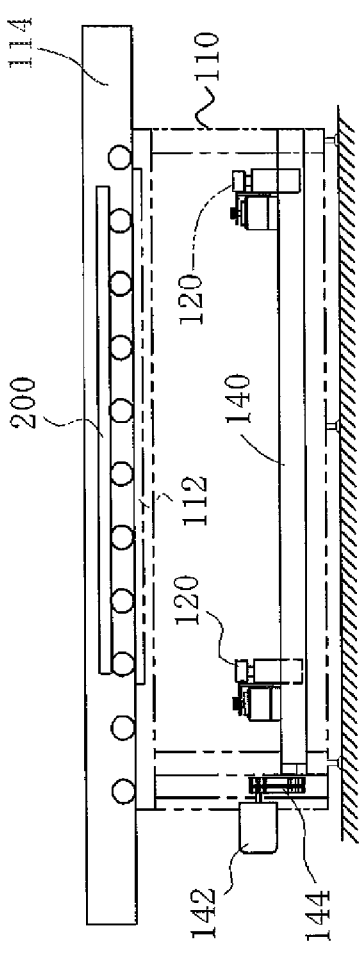

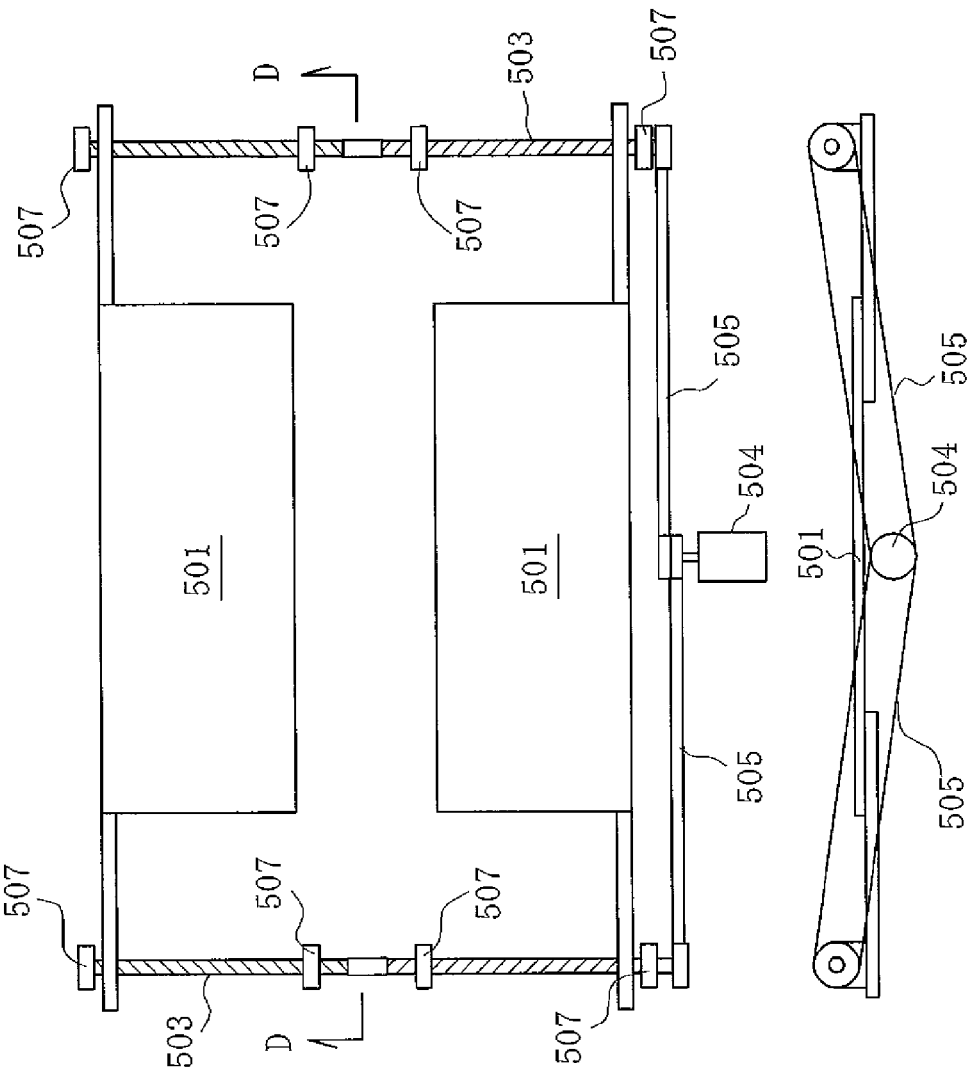

INSPECTING APPARATUS FOR PHOTOVOLTAIC DEVICES

PRIORITY CLAIM

The present specification claims priority from Japanese Patent Application No. 2007-273538, filed on Oct. 22, 2007 in Japan Patent Office, the entire contents of which are hereby incorporated by reference herein.

BACKGROUND OF THE INVENTION

1. Field of the Invention

The present invention relates to an inspecting apparatus which is employed to inspect general performance of a photovoltaic devices, such as a photovoltaic cell, a photovoltaic string which is formed by connecting the photovoltaic cells in series, a photovoltaic devices panel which is formed by disposing a plurality of photovoltaic strings in parallel, and the like.

2. Description of the Background Art

It is well known that a silicon photovoltaic devices is employed to harness solar energy. In the manufacture of the photovoltaic devices, it is important to evaluate whether the photovoltaic devices has predetermined power generation capacity. The evaluation is usually performed by measuring output characteristics thereof.

The output characteristics is the photovoltaic conversion characteristics obtained by measuring current-voltage characteristics of photovoltaic devices under light irradiation. As a light source, it is desired to use the solar light. However, since the intensity of the solar light varies in relation to weather, a solar simulator is employed. In the solar simulator, a xenon lamp, a metal halide lamp or the like is employed as an alternative to the solar light. If the aforementioned light source has been lighted for a long time, the temperature thereof rises or the like, leading to a variation on the light intensity thereof. Therefore, by using the flash light of the aforementioned light source, it is able to plot the output characteristic curve of the photovoltaic devices on the basis of collected data with setting a voltage as the lateral axis and a current as the vertical axis (for example, refer to Japanese Patent Application Laid-Open No. 2007-88419).

The following different method from the solar simulator is disclosed in the Patent Document WO/2006/059615. By applying a voltage to a polycrystalline silicon photovoltaic devices element in a forward direction. The photovoltaic devices element emits electro-luminescence light (hereinafter referred to simply as a "EL light"). The photovoltaic devices element is inspected thereby. By studying the EL light emitted from the photovoltaic devices element, it is able to obtain the distribution of the current density of the photovoltaic devices element. The defects of the photovoltaic devices element can be found out on the basis of the uneven distribution of the current density. Namely, a portion which emits no EL light is decided to be a defective portion and the photovoltaic devices element can be decided to have the predetermined power generation capacity if the total area of the defective portions is smaller than a predetermined amount.

The structure of the inspecting apparatus described in the Patent Document WO/2006/059615 is schematically illustrated in FIG. 9. An inspecting apparatus 10 includes a darkroom 11, a CCD camera 12 which is disposed at an upper portion of the darkroom 11, a power source 14 which applies current to a photovoltaic cell 13 disposed on the floor of the darkroom 11, and an image processing apparatus 15 which processes image signals from the CCD camera 12.

The darkroom 11 is provided with a window 11a where a finder 12a of the CCD camera 12 is disposed. Therefore, an image to be photographed by the CCD camera 12 can be confirmed by watching with eyes from the finder 12a. As the image processing apparatus 15, a computer is employed.

In the inspecting apparatus 10 illustrated in FIG. 9, the photovoltaic devices cell 13 is disposed at a lower side of the darkroom 11 and is photographed by the camera from an upper side thereof. However, since the EL light emitted from the photovoltaic cell 13 is a weak light ray of wavelength between 1,000 nm and 1,300 nm, it is not able to be detected unless the photovoltaic cell is disposed inside the darkroom 11. In the case that the inspecting object is a piece of photovoltaic cell, the size thereof is about 100 mm×100 mm, which is possible to be disposed in a small-sized darkroom.

However, in the case that the inspecting object is a photovoltaic devices panel, the size thereof is about 2 m×1 m; therefore, the darkroom 11 has to have a dimension capable of disposing the photovoltaic devices panel. Further, the photovoltaic devices panel as the inspecting object has to be disposed inside the darkroom so as to be photographed by the CCD camera 12. Therefore, a door has to be provided in the darkroom so as to transport the photovoltaic devices panel into or carry out from the darkroom. If the inspecting apparatus is configured so as to transport the inspecting object into the darkroom, in the case that the disposed door is closed, shading effect has to be secured. It is also necessary that the inspecting apparatus is provided with a positing member and a guide member for transporting the photovoltaic devices in the darkroom of the inspecting apparatus. Furthermore, it is also necessary that the inspecting apparatus is provided with an electrifying means for applying a current to the photovoltaic devices in the darkroom. Thereby, the darkroom becomes complicated in structure and expensive in price.

SUMMARY OF THE INVENTION

The present invention has been accomplished in view of the aforementioned problems, and it is, therefore, an objective of the present invention to provide a cheap and simple-structured inspecting apparatus to make the photovoltaic devices emit EL light by applying a current to the photovoltaic devices in a forward direction.

To attain the objectives described above, the inspecting apparatus for photovoltaic devices according to the present invention includes: a darkroom having a flat upper surface; a transparent plate which is provided in the upper surface of the darkroom for disposing the photovoltaic devices as an inspecting object; and a camera which is provided in the darkroom.

The configuration can be employed that the inspecting apparatus is provided with a driving mechanism to move the camera in the darkroom.

The configuration can be employed that the inspecting apparatus is provided with a shading means to shade light rays entering the darkroom through a gap in the boundary between the transparent plate and the photovoltaic devices disposed on the transparent plate. The configuration can be employed that the inspecting apparatus is provided with a guide member having a shading means on the upper surface for guiding the photovoltaic devices during transporting into the inspecting apparatus.

According to the inspecting apparatus for the photovoltaic devices of the present invention, by disposing the photovoltaic devices as the inspecting object on the transparent plate in the upper surface of the darkroom from the outside of the darkroom, it is possible to use the camera in the darkroom to photograph the photovoltaic devices. Since the photovoltaic devices is applied with a current during photographing, the photovoltaic devices emits EL light. The state of emitting EL light of the photovoltaic devices is photographed by the camera. According to the analysis performed by the image processing apparatus which is connected with the camera, it is possible to inspect out whether the photovoltaic devices has a defect or not.

The photovoltaic devices can be inspected by disposing it on the upper surface of the darkroom from the outside of the darkroom; therefore, it is not necessary to provide a door for transporting the photovoltaic devices as the inspecting object into or carrying out of the darkroom. Accordingly, it is possible to simplify the structure of the darkroom, thereby, enabling miniaturization thereof.

Further, in the case that the inspecting object is the photovoltaic devices panel, the photovoltaic devices panel is transported in a manufacturing line (manufacturing apparatus, such as a laminating apparatus) with the state that receiving light side faces downward. Since the inspecting apparatus of the present invention is provided with a transparent plate on the upper surface of the darkroom, it is possible to dispose the photovoltaic devices panel on the inspecting apparatus without inversing it.

Other features and advantages of the present invention will be apparent from the following description when taken in conjunction with the accompanying drawings, in which like reference characters designate similar or identical parts throughout the several views thereof.

BRIEF DESCRIPTION OF THE DRAWINGS

FIG. 1A is a planar view illustrating an inspecting apparatus for a photovoltaic devices according to the present invention;

FIG. 1B is a sectional view along B-B line in FIG. 1A;

FIG. 1C is a right-side view illustrating the inspecting apparatus according to the present invention;

FIG. 2A is a planar view illustrating a configuration of a camera and a drive mechanism for the camera of the inspecting apparatus for the photovoltaic devices according to the present invention;

FIG. 2B is a front view of FIG. 2A;

FIG. 2C is a right-side view of FIG. 2A;

FIG. 6A is a planar view illustrating a driving mechanism of the shading means in FIG. 5A and FIG. 5B;

FIG. 6B is a left-side view of FIG. 6A;

FIG. 6C is a sectional view along D-D line in FIG. 6A;

DETAILED DESCRIPTION OF THE INVENTION

Hereinafter, embodiments according to the present invention is described with reference to the accompanying drawings. In so doing, specific terminology is employed solely for the sake of clarity, and the present disclosure is not to be limited to the specific terminology so selected. It is to be understood that each specific element includes all technical equivalents that operate in a similar manner and achieve a similar result.

1. Inspecting Object: Photovoltaic Module

Figure 8A:
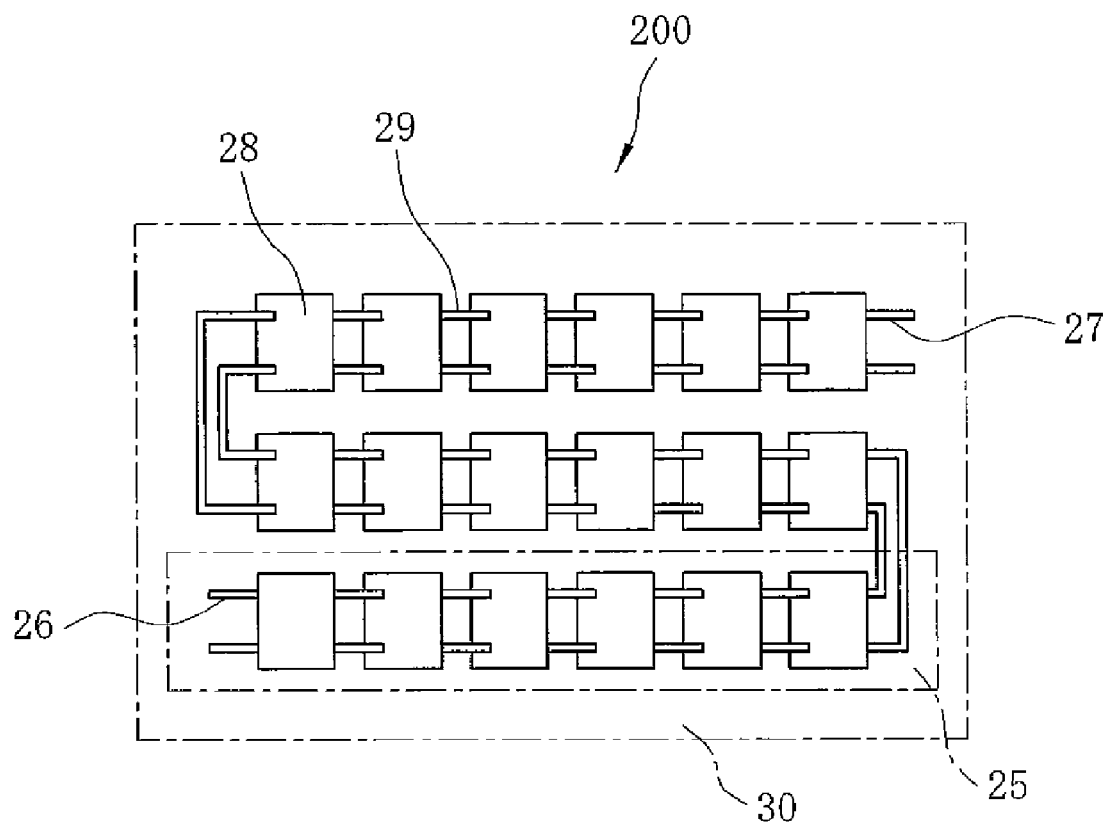
FIG. 8A is a planar view explaining a configuration of the photovoltaic devices being inspected by the inspecting apparatus of the present invention.
Figure 8B:
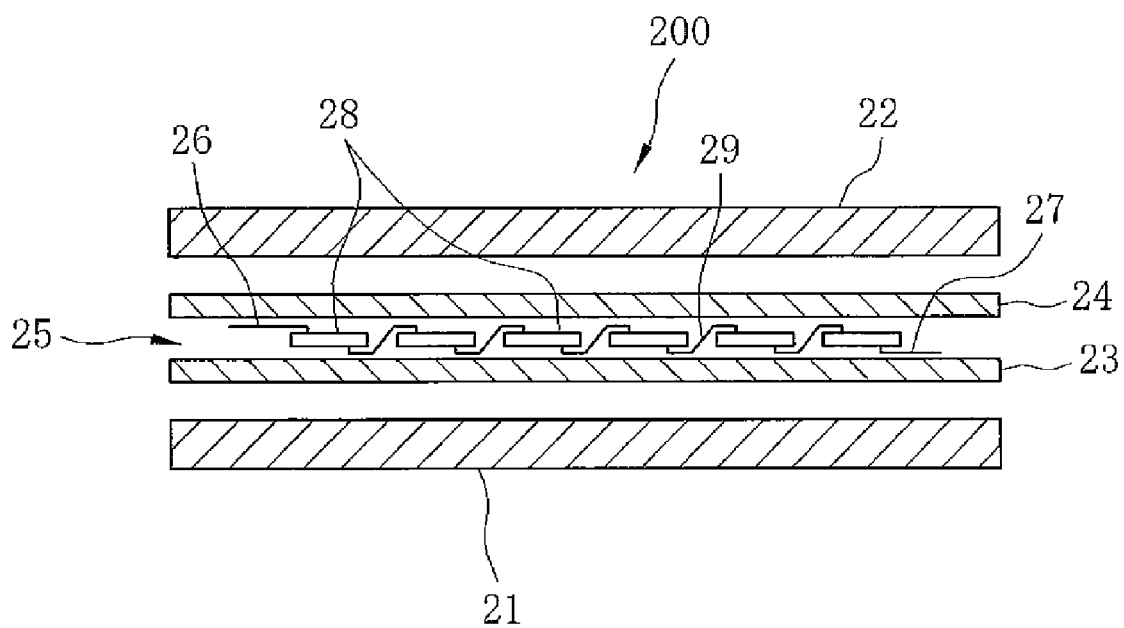
FIG. 8B is a sectional view thereof.

First, description is given of an example of an inspecting object 200 which is inspected by an inspecting apparatus of the present invention. FIG. 8A is a planar view explaining a configuration of the photovoltaic devices being inspected by the inspecting apparatus of the present invention; and FIG. 8B is a sectional view of FIG. 8A. In FIG. 8A, photovoltaic cells in the photovoltaic devices are clearly illustrated.

As illustrated in the planar view of FIG. 8A, the photovoltaic module (namely the inspecting object 200) is formed in the following way:

Plural square photovoltaic cells 28 are connected in series by lead wires 29 to form a string 25. Further plural columns of strings 25 are connected by lead wires 29 to form the photovoltaic module.

The photovoltaic devices as the inspecting object 200 may be formed from a single photovoltaic cell 28 only, or may be formed from the string 25 in which the plural photovoltaic cells 28 are straightly connected, or may be a photovoltaic devices panel 30 in which the plural columns of strings 25 are disposed in parallel and the photovoltaic devices cells 28 are disposed in matrix.

As illustrated in FIG. 8B, the configuration of the inspecting object in section structure is formed by disposing the plural columns of strings 25 sandwiched by filling members 23 and 24 between a back side member 22 disposed in an upper side and a transparent cover glass 21 disposed in a lower side.

The back side member 22 is made of, for example, polyethylene resin or the like. The filling members 23 and 24 are made of, for example, EVA resin (polyethylene vinyl acetate resin). As described above, the string 25 is formed by connecting the photovoltaic cells 28 with lead wires 29 between electrodes 26 and 27.

The photovoltaic devices module is obtained by piling the aforementioned constructional members and laminating. The laminating process is performed by pressing with force under heating in vacuum to cross-link the EVA resin with a laminator or the like.

Moreover, a kind of photovoltaic devices, which is generally called as a thin film-type, may be employed as the inspecting object 200.

For example, a typical structure of this thin film-type photovoltaic devices is obtained in the following way:

depositing a power generating element comprised of a transparent electrode, a semiconductor and a rear back electrode via vacuum evaporation on the transparent cover glass disposed at the lower side; disposing the transparent cover glass at the lower side; covering the photovoltaic devices elements disposed on the glass with the filling members; covering the filling members with the back side member; and laminating the piled constructional members with a laminator.

This kind of the thin film-type photovoltaic module serving as the inspecting object 200 only replaces crystalline cells with the aforementioned power generating elements, and the basic sealing structure is identical to the case of the crystalline cells in the aforementioned description.

2. Entire Configuration of the Inspecting Apparatus

FIG. 1A is a planar view illustrating an inspecting apparatus for a photovoltaic devices according to the present invention; FIG. 1B is a sectional view along B-B line in FIG. 1A; and FIG. 1C is a right-side view illustrating the inspecting apparatus according to the present invention. FIG. 2A is a planar view illustrating a configuration of a camera and a drive mechanism for the camera of the inspecting apparatus for the photovoltaic devices according to the present invention; FIG. 2B is a front view of FIG. 2A; and FIG. 2C is a right-side view of FIG. 2A.

The inspecting apparatus 100 for the photovoltaic device according to the present invention, as illustrated in the drawings, has a cubic box-shaped darkroom 110. A transparent plate 112 is disposed at a flat upper surface 111 thereof. The transparent plate 112 is made of synthetic resin such as acryl resin or of glass. A camera 120 for inspecting the photovoltaic devices serving as the inspecting object 200, and a moving mechanism thereof are disposed in the darkroom. Note that it is possible to dispose only the camera in the darkroom without the moving mechanism according to the usage. The upper surface 111 is made of shading materials to prevent light rays from entering the darkroom 110, except the transparent plate 112. It is also possible to make the entire upper surface 111 into a transparent plate if the photovoltaic devices as the inspecting object 200 is disposed on the upper surface 111 and then the entire upper surface 111 including the inspecting object 200 is further covered with a shading means. Except the upper surface 111, the other 4 side surfaces and the bottom surface are comprised of shading member. Further, the upper surface 111 is provided with a pair of guide members 114, 114 to guide the inspecting object 200 during transporting into the inspecting apparatus. The distance between a pair of guide members 114, 114 is adjusted according to the dimension of the inspecting object 200.

3. Guiding the Inspecting Object 200 for Transportation and Positioning

The guide member 114 is a narrow and long rail having a cross section of a rectangular shape. On the upper surface 111 of the inspecting apparatus 100 according to the present invention, a pair of the guide members 114 are disposed along a direction of transporting the inspecting object 200. On the inner side surface of each guide member 114, plural rollers 115 are disposed. The inspecting object 200 is transported by the plural rollers 115. Therefore, during transportation and inspection of the inspecting object 200, the cover glass 21 at the lower side does not have contact with the transparent plate 112 in the upper surface 111 of the inspecting apparatus 100. According to the dimension of the inspecting object 200, the guide member 114 is adjusted through a moving rail 116, feeding screws 117 which are disposed at a transporting-in side and a carrying-out side of the inspecting apparatus and a handle 118. Namely, the each feeding screw 117 on both sides is comprised of 2 screws. One of the screw 117 is a right-hand screw and the other is a left-handed screw. By rotating the handle 118, the guide members 114 and 114 move closely to each other or separately from each other with the center position between one guide members 114 and the other guide members 114 being maintained. Furthermore, the feeding screws 117 in the transporting-in side and the carrying-out side are connected through a cross shaft 113 having bevel gears. When the handle 118 is rotated, the feed screws 117 on both sides can rotate simultaneously through the bevel gears.

One side surface of the guide member 114 is provided with positioning member 119, which is protruded and withdrawn from the inner side of guide member 114 by use of an actuator or the like. The position of the transported inspecting object 200 is positioned in the transportation direction by protruding the positioning member 119. The positioning member 119 can not only be configured as being protruded and withdrawn from the inner side of the guide member 114, but also can be configured as ascending and descending from an upper position of the guide member, or being rotated downward from the guide member.

4. Photographing Camera

The EL light emitted from the inspecting object 200 is a weak light ray of wavelength between 1,000 nm and 1,300 nm, is emitted in the darkroom 110 and the weak light ray is photographed by using the photographing camera 120. Therefore, it is necessary to use a CCD camera which has high sensitivity to weak light as the photographing camera 120. In the present embodiment, a Si-CCD camera of Model C9299-02 manufactured by Hamamatsu Photonics K. K. is employed.

5. Moving Mechanism for the Camera in the Darkroom

The configuration of the moving mechanism for the camera is illustrated in FIG. 2A, FIG. 2B and FIG. 2C. The darkroom 110 is provided with the camera 120, and a Y axis guide part 130 for moving the camera 120 in Y axial direction. A motor 132 is disposed at one end of the Y axis guide part 130. The camera 120 is moved forward or backward along the Y axial direction according to the rotation of the motor 132.

Both ends of the Y axis guide part 130 are supported by X axis guide part 140 and 140, respectively. The Y axis guide part 130 can be moved forward or backward on the X axis guide part 140 and 140 along the X axial direction by a motor 142 and a timing belt 144 on both sides. In the aforementioned configuration, the X axis guide part 140 and 140, the Y axis guide member 130, the motors 132 and 142, and the timing belt 144 constitute the driving mechanism for the camera 120. It is possible for the X axis guide part 140, 140 and the Y axis guide part 130 to use various types of linear actuators. In the present embodiment, a ball screw is employed.

By controlling the rotations of the motors 132 and 142 of the driving mechanism, the camera 120 can be moved to an arbitrary position in X-Y plane so as to make it possible to photograph at an arbitrary position on the inspecting object 200.

The driving means is not limited to the aforementioned embodiment such that a motor and a ball screw are employed. Various types of linear actuators can be employed.

6. The Other Instruments

Figure 9:
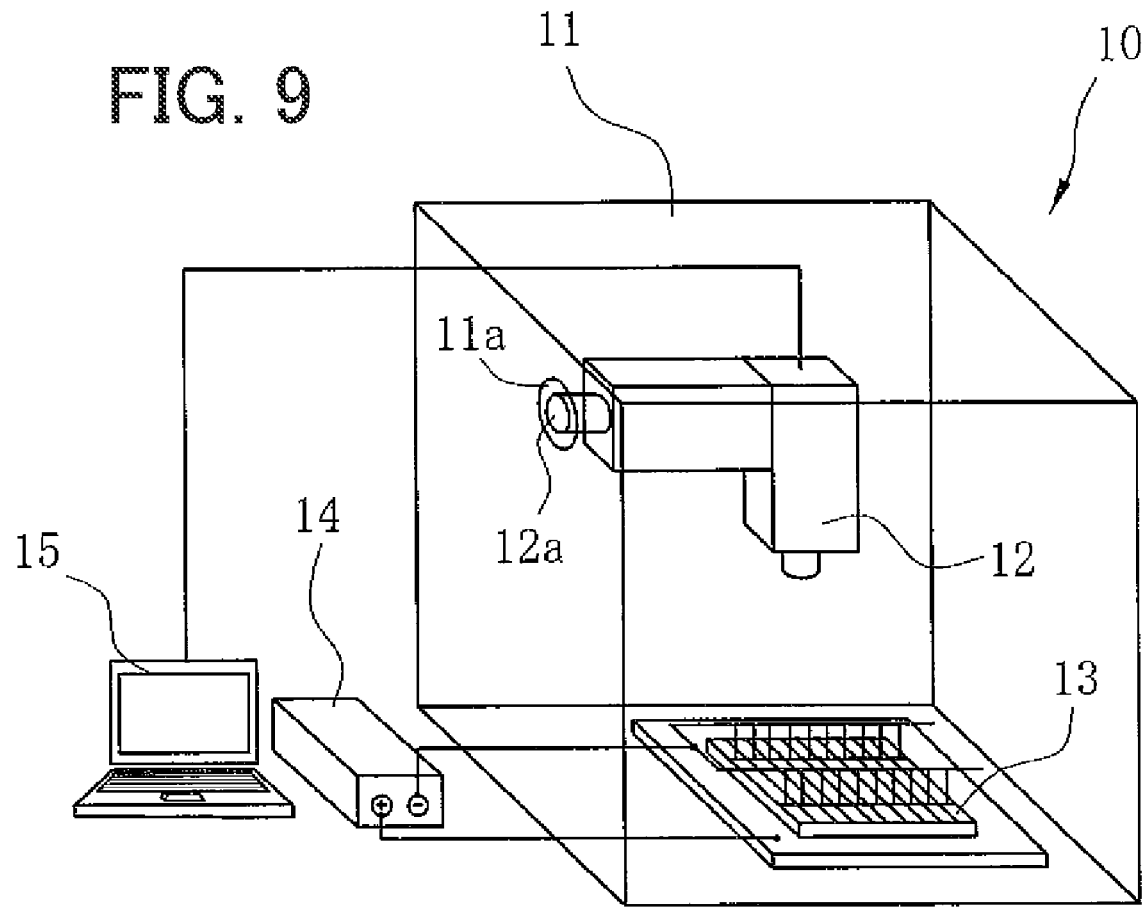
FIG. 9 is a view schematically illustrating a configuration of a conventional inspecting apparatus for photovoltaic devices.

In addition to the aforementioned means, although not illustrated in the drawings, the inspecting apparatus 100 of the present invention is provided with a power source 14 and an image processing apparatus 15 in which a computer is employed as conventional inspecting apparatus illustrated in FIG. 9.

7. Usage of the Inspecting Apparatus

A description is given of the usage of the inspecting apparatus for the photovoltaic devices of the present invention in the example in which the photovoltaic device panel is employed as the inspecting object 200.

After the photovoltaic devices panel manufactured in a laminator or the like is carried out, it is transported by the conveyor or the like in front of the inspecting apparatus for the photovoltaic devices of the present invention. The transported photovoltaic devices panel is guided by the pair of guide members 114, 114 to move on the rollers 115 provided at the inner side of the guide members, and reaches the upper surface of the darkroom 110. Thereafter, photovoltaic devices panel is positioned in the direction of transporting by protruding the positioning member 119 disposed at the inner side of the guide member 114 in the manner that the positioning member 119 is protruded and withdrawn by an actuator or the like.

The photovoltaic devices panel as the inspecting object 200 reaches a predetermined position of the darkroom 110, then stops on the transparent plate 112 of the darkroom 110 with the transparent glass plate disposed at the lower side and is connected with a power source not shown in drawings. Since the inspecting object 200 is smaller than the transparent plate 112, light rays enter the darkroom from the boundary between the inspecting object 200 and the transparent plate 112. Therefore, a shading means which is described hereinafter is disposed to cover the entire upper portion of the darkroom 110 from the upper side of the inspecting object 200. The power source electrifies the inspecting object 200 in a forward direction to make the inspecting object 200 emit EL light, which is photographed by the camera 120.

In the case that the inspecting apparatus 100 of the present invention is employed to photograph the entire part of the inspecting object 200 and inspect the photovoltaic devices by the obtained image, it is possible to fix the camera 120 on the floor of the darkroom 110 without the necessity of being provided with the moving mechanism. In this case, the inspecting object 200 may be any one of the photovoltaic cell 28, the photovoltaic devices string 25 which is formed by connecting plural photovoltaic cells 28 with lead wires, and the photovoltaic devices panel 30 in which the plural columns of strings 25 are disposed in parallel and the photovoltaic cells 28 are disposed in matrix.

In the case that the inspecting apparatus 100 of the present invention is employed to photograph the respective photovoltaic cells 28 disposed in matrix in the photovoltaic devices panel 30 and inspect by the obtained images, the moving mechanism is disposed so as to move the camera 120 in the darkroom 110.

By controlling the rotation of the motors 132 and 142 in the driving mechanism, the camera 120 photographs respective photovoltaic cells 28 disposed in matrix in the photovoltaic devices panel 30, and the obtained image data is transmitted to the image processing apparatus (not shown in drawings) comprised of a computer and the like. The image processing apparatus extracts those portions which emit no EL light from the image of respective photovoltaic cells and analyze. Whether the respective photovoltaic cells 28 is passed or not is decided on the basis of the obtained image data of respective photovoltaic cells. Whether the photovoltaic devices panel 30 as a whole is passed or not is decided on the basis of the analyzed results for all photovoltaic cells.

Respective photovoltaic cells or every few pieces of photovoltaic cells may be photographed by moving the camera and the photovoltaic devices panel 30 as a whole may be photographed by fixing the camera without moving.

8. Shading Means

In the description above, it is described that the shading means cover the entire upper surface 111 of the darkroom 110. However in the case of the photovoltaic devices panel 30, the back side member 22 made of resin at the back side is not transparent and has sufficient shading effect. Moreover, the upper surface 111 of the darkroom 110 is comprised of members having shading effect, except the transparent plate 112. In the case that the inspecting object 200 is disposed in close contact with the transparent plate 112 and larger than the transparent plate 112, the inspecting object 200 covers the entire transparent plate 112. Therefore, the shading means is not necessary.

However, in the case that the inspecting object 200 is smaller than the transparent plate 112 or is floated from the transparent plate 112 for light rays to enter the darkroom 110 from the gap, it is therefore necessary to cover the upper surface of the darkroom with shading means. The shading means is described in detail hereinafter.

8-1. Embodiment 1 of the Shading Means

Figure 3:
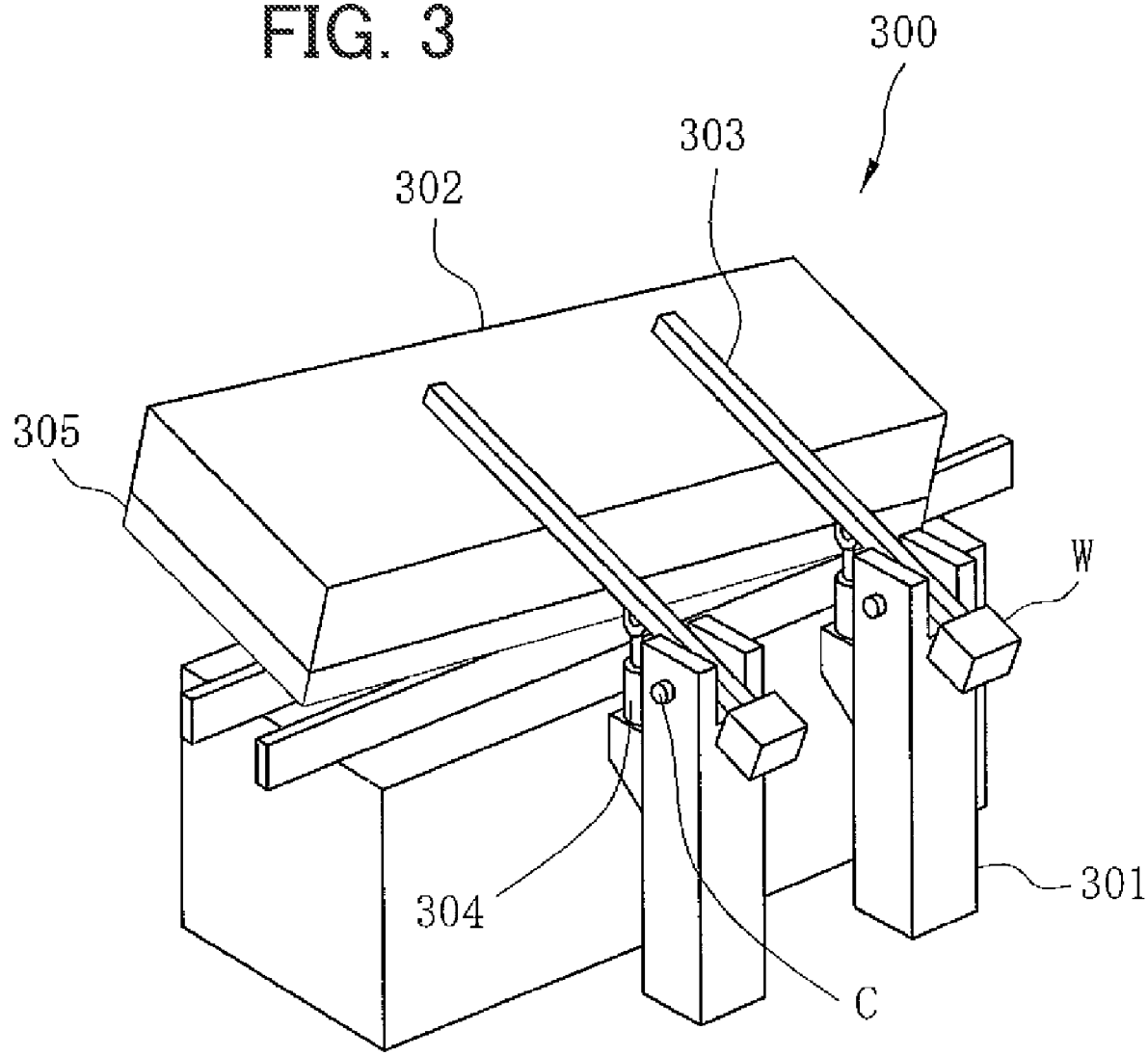
FIG. 3 is a perspective view illustrating Embodiment 1 of a shading means of the inspecting apparatus according to the present invention.

In the present embodiment, the shading means is configured as a shading member 302 to covers the entire upper surface 111 of the darkroom 110, as illustrated in FIG. 3. One side in the direction of width of inspecting apparatus 100 of the present invention is provided with a base 301 of the shading means 300. The shading member 302 is configured as follows. The shading member 302 is supported by two arms 303. The arms 303 are respectively rotated by two air cylinder 304 around a rotating central axis C so as for the shading member 302 to ascend and descend.

Reference number W in FIG. 3 denotes a counter weight when the shading member 302 rotates ascends and descends. The shading member 302 is closed (descended) while the inspecting object 200 is inspected. The shading member 302 is opened (ascended) while the inspecting object 200 is transported into the inspecting apparatus 100.

The shading member 302 is a box with the lower side thereof opened, which is made of thin plates such as steel. A shading sheet 305 made of rubber is fixed in the lower part of four side of the shading member 302 to ensure shading effect.

The shading sheet 305 may be configured by binding strip-like cloth having light shading effect into a bundle similar to the end of a cleaning mop. The shading sheet 305 may be also configured by implanting fibers having shading effect into a brush-like member The vertical movement of the shading member 302 is not limited to ascending and descending vertically through rotation as described in the present embodiment. Although not shown in the drawings, by being provided with poles at each of four corners of the inspecting apparatus 100 for guide the shading member 302, the shading member 302 may ascend and descend vertically with an actuator.

8-2. Embodiment 2 of the Shading Means

Figure 4A:
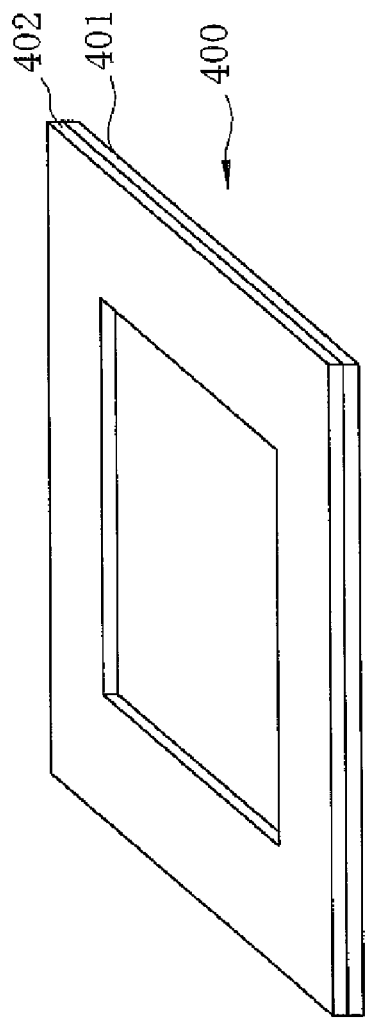
FIG. 4A is a perspective view illustrating a configuration of Embodiment 2 of a shading means of the inspecting apparatus according to the present invention.
Figure 4C:
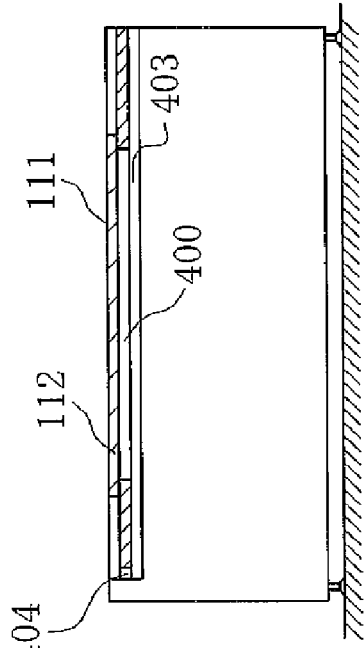
FIG. 4C is a sectional view along C-C line in FIG. 4B.
Figure 4B:
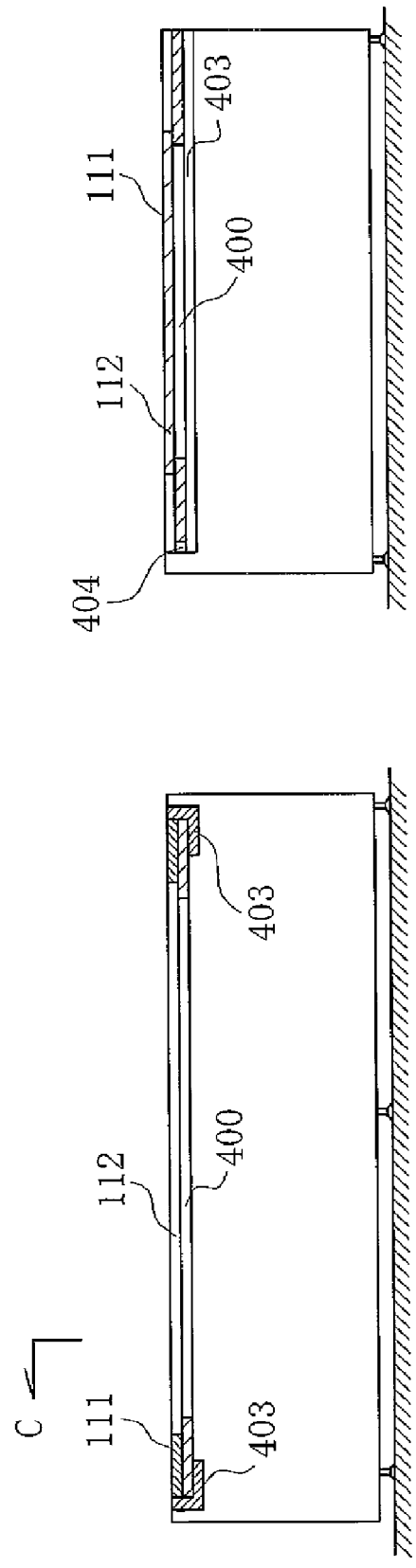
FIG. 4B is a sectional view illustrating the attached state of the shading means.

FIG. 4A is a perspective view illustrating a configuration of Embodiment 2 of the shading means of the inspecting apparatus according to the present invention; FIG. 4B is a sectional view illustrating the attached state of Embodiment 2 of the shading means; and FIG. 4C is a sectional view along C-C line in FIG. 4B.

The shading means 400 in FIG. 4A to prevent light rays from entering through a frame-like gap between the transparent plate 112 and the inspecting object 200 is configured by attaching a sponge 402 or the like having shading effect to a rigid plate 401 made of metal, resin or the like. The sponge 402 is disposed on the surface contacting the transparent plate 112. It is acceptable for the shading means 400 to have a dimension of shading means which can at least cover the frame-like gap between the transparent plate 112 and the inspecting object 200.

In the present embodiment, as illustrated in FIG. 4B, the back side of the upper surface 111 of the inspecting apparatus 100 is provided with a pair of L-shaped metal rail members 403, 403. The frame-like shading means 400 as illustrated in FIG. 4A is inserted between the pair of metal rail members 403, 403. One end of the metal rail member 403 is provided with a stopper 404 to position the shading means 400. The sponge 402 is in close contact with the transparent plate 112. One side surface of the darkroom 110 of the inspecting apparatus 100 is open-able and closable so as to exchange the shading means 400 according to the dimension of the inspecting object.

8-3. Embodiment 3 of the Shading Means

The present embodiment is a alternative example to Embodiment 2 of the shading means, which is employed in the case that the dimension of the inspecting object 200 is changed in a small lot. The shading means 500 is comprised of shading plates in 2 pairs (totally 4 shading plates) which are automatically moved by an actuator according to the dimension of the inspecting object 200.

Figure 5A:
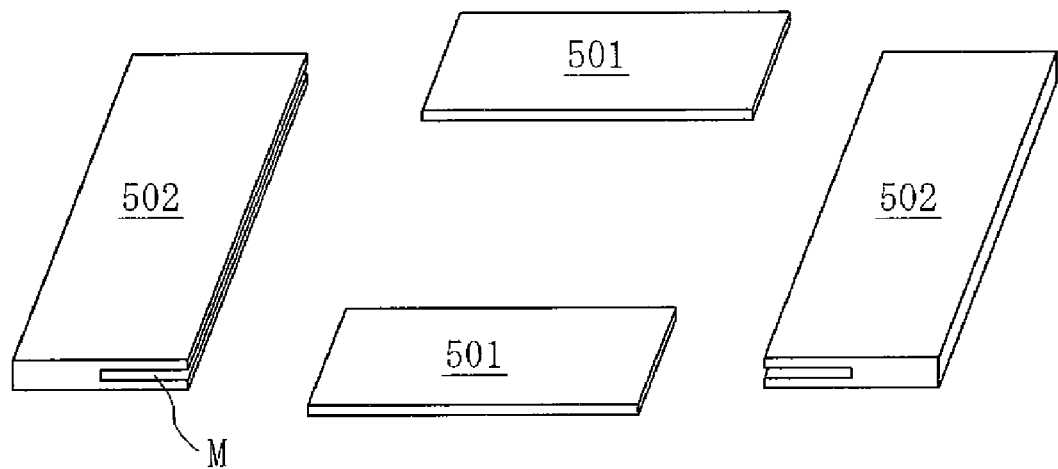
FIG. 5A is a perspective view illustrating an disassembled state of Embodiment 3 of the shading means of the inspecting apparatus according to the present invention.

The configuration thereof is described with reference to FIG. 5A and FIG. 5B. The frame-like shading plate illustrated in FIG. 4A is divided into one pair of the shading plates 501, 501 and the other pair of the shading plates 502, 502 totally 4 plates, as illustrated in FIG. 5A. Similar to Embodiment 2 as illustrated in FIG. 4A, the 2 pairs of the shading plates 501 and 502 are disposed on the back side of the upper surface 111 of the inspecting apparatus 100. Each shading plate 501 is a rectangular plate having shading effect. Each shading plates 502 is provided with a groove M into which the shading plates 501 are fitted by sliding.

Figure 5B:
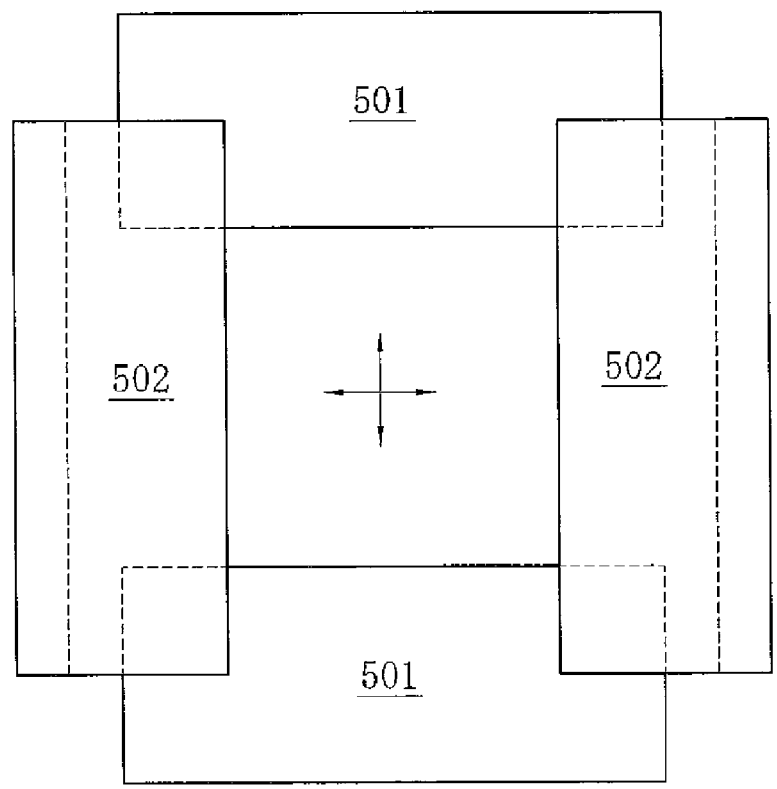
FIG. 5B is a planar view illustrating an assembled state of FIG. 5A.

As illustrated in FIG. 5B, the shading plates 501 and 502 are disposed. An opening size of the shading plates 501 and 502 is varied according to the dimension of the inspecting object 200 by moving each pair of shading plates 501 and 502 closely to or separately from each other, respectively.

FIG. 6A, FIG. 6B and FIG. 6C illustrate the driving mechanism for varying the opening size of the shading plates 501 and 502 in FIG. 5A and FIG. 5B. FIG. 6A is a planar view thereof; FIG. 6B is a left-side view thereof; and FIG. 6C is a sectional view along D-D line in FIG. 6A.

As illustrated in the drawings, the pair of shading plates 501 are connected by two screws 503, 503 which are disposed laterally on both sides thereof, respectively. One of the screws 503 is comprised of a right-hand screw and a left-hand screw. The two screws 503, 503 on both sides are rotated by a motor 504 via timing belts 505 and 505, respectively. Eight brackets 507 which support the two screws 503 and the motor 504 are fixed at appropriate locations of the inspecting apparatus 100. The pair of shading plates 501 can be moved closely to or separately from each other according to the rotation of the motor 504. The position of each shading plate 501 is confirmed by an encoder not shown in drawings. Although it is not illustrated in the drawings, the configuration of the driving mechanism of the shading plates 502 and 502 is the same as that of the shading plates 501 and 501. By the aforementioned configuration, an opening size thereof may be varied according to the dimension of the inspecting object 200.

8-4. Embodiment 4 of the Shading Means

Figure 7A:
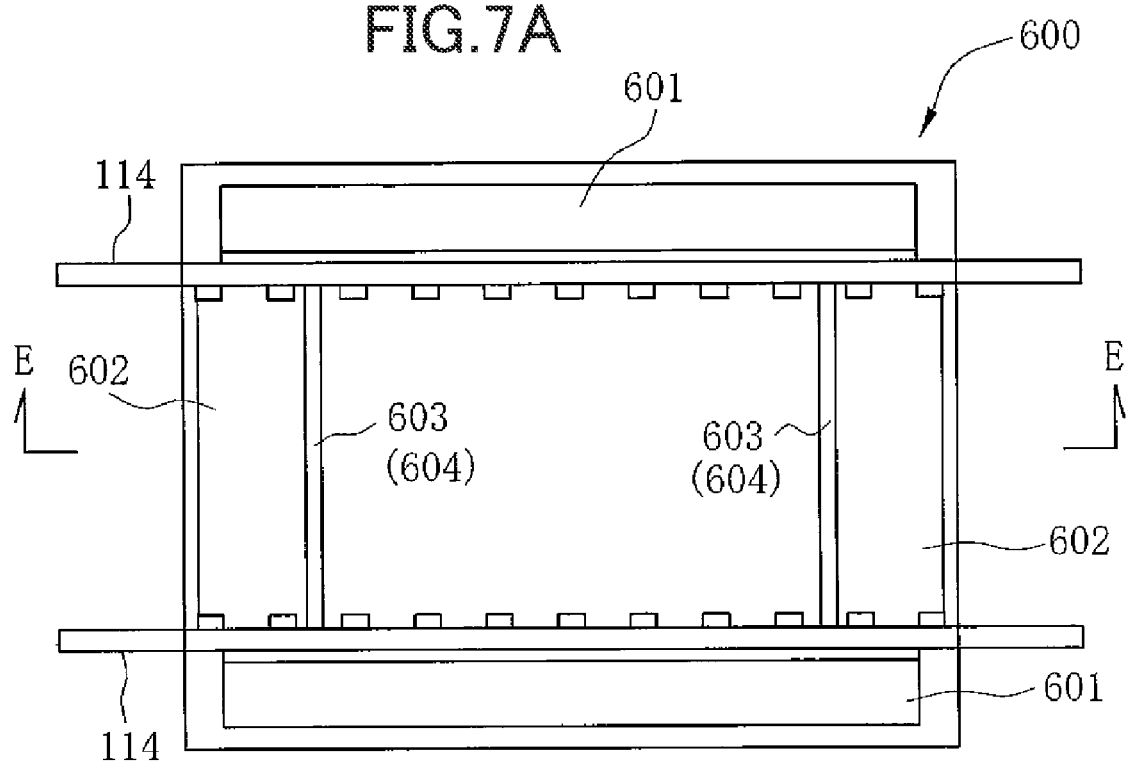
FIG. 7A is a planar view illustrating Embodiment 4 of the shading means of the inspecting apparatus according to the present invention provided in a guide member for guiding the photovoltaic devices during transporting.
Figure 7B:
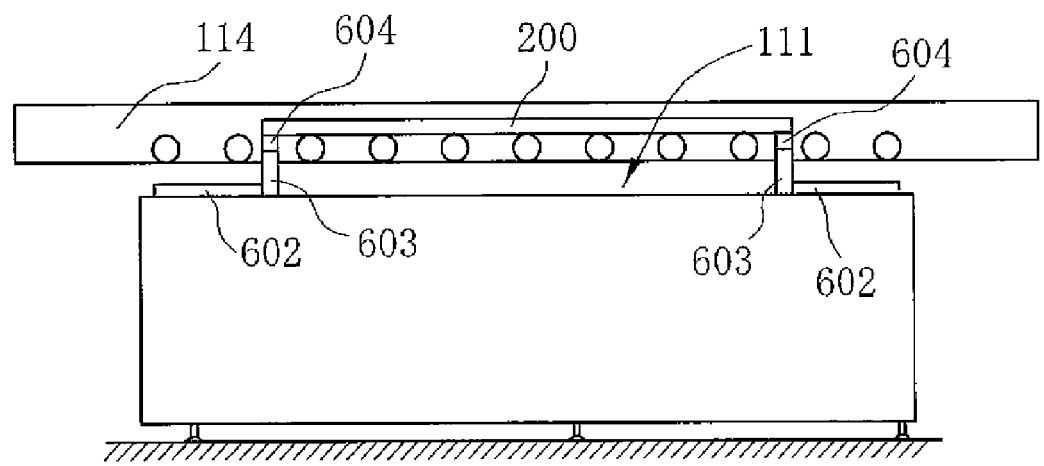
FIG. 7B is a sectional view along E-E line in FIG. 7A.

The shading means of the present embodiment is employed to prevent light rays from entering through the boundary between the transparent plate 112 and the inspecting object 200. In the present embodiment, the shading means 600, which is described hereinafter, is provided in the pair of guide members 114 which guide the photovoltaic devices during transporting into the inspecting apparatus 100, as illustrated in FIG. 7A and FIG. 7B.

The shading sheet 601 is attached to the outer side of each of the pair of guide members 114. The shading sheet 601 is a rubber-like sheet having shading effect. The shading sheet 601 is disposed as sagging downward from the guide member 114 and covering over the boundary between the transparent 112 and the upper surface 111 of the inspecting apparatus 100 with the sagged part. Light rays entering from the gap in the direction of transporting of the inspecting object 200 of the frame-like gap can be shaded by the shading sheet 601. On the other hand, the gap in the vertical direction to the direction of transporting of the inspecting object 200 includes the gap of the transporting-in side and the gap of the carrying-out side of the inspecting apparatus. A rectangular shading plate 602 is provided at the transporting-in side and the carrying-out side between the pair of guide members 114. Since the shading plate 602 is also disposed at the transparent plate 112, it is desired that the shading plate 602 is made of hard rubber having shading effect so that it does not damage the transparent plate 112. Moreover, since there is a distance from the transparent plate 112 of the darkroom 110 to the inspecting object 200, the shading plate 602 is connected with a pair of shading block-like members 603. The part of the pair of block-like members 603 having contact with the inspecting object 200 is attached with a sponge-like member 604 which has flexibility and shading effect. The block-like members 603 are pressed to have contact with the inspecting object 200, and can shade light rays thereby. Accordingly, the gap in the vertical direction to the direction of transporting of the inspecting object 200 (namely the gaps in the transporting-in side and the carrying-out side of the inspecting apparatus 100) is shaded. According to the aforementioned configuration, shading means 600 is comprised of the shading sheet 601, the shading plate 602, the block-like members 603 and the sponge-like members 604.

In the present invention, it is acceptable to use the shading means in Embodiments 1 to 4 respectively; it is also possible to use a combination of plural shading means in Embodiments 1 to 4 so as to improve the shading effect.

In the inspecting apparatus 100 for the photovoltaic devices according to the present invention, since the photovoltaic devices may be disposed outside the darkroom, it is not necessary to be provided with a door in the darkroom for transporting the inspecting object 200 in or carrying out of the darkroom. Moreover, the power source and wires for applying current to the photovoltaic devices may be disposed outside the darkroom 110, without the necessity of disposing them therein. Thereby, the structure of the darkroom can be simplified.

The inspecting apparatus 100 for photovoltaic devices of the present invention can be installed for use in a manufacturing process for manufacturing a photovoltaic devices panel or the like. In this case, the photovoltaic devices panel is disposed on the upper surface 111 of the darkroom 110 with the receiving light side facing downward. In a common manufacturing process, such as the laminating process or the like of the photovoltaic devices panel, the photovoltaic devices panel is transported with the receiving light side facing downward. Therefore, there is no need to inverse the photovoltaic devices panel when disposing it on the inspecting apparatus 100. Accordingly, the manufacturing process can be simplified.

As many apparently widely different embodiments of the present invention can be made without departing from the spirit and scope thereof, it is to be understood that the invention is not limited to the specific embodiments thereof except as defined in the appended claims.

What is claimed is:

1. An inspecting apparatus for photovoltaic devices, comprising:
    a darkroom having a flat upper surface;
    a transparent plate provided on the upper surface of the darkroom for disposing the photovoltaic devices as an inspecting object; and
    a camera provided in the darkroom.

2. The inspecting apparatus according to claim 1, wherein the darkroom is provided with a driving mechanism configured to move the camera therein.

3. The inspection apparatus according to claim 1, further comprising shading means configured to prevent light rays from entering the darkroom through a gap between the transparent plate and the photovoltaic devices disposed on the transparent plate.

4. The inspection apparatus according to claim 1, wherein a guide member having shading means and configured to guide the photovoltaic devices during transport is provided on the upper surface.

* * * * *